United States Patent [19]

Evans

[11] Patent Number: 4,499,285

[45] Date of Patent: Feb. 12, 1985

[54] SOLVENT FREE PREPARATION OF DIARYLTHIOETHERS

[75] Inventor: Thomas L. Evans, Schenectady, N.Y.

[73] Assignee: General Electric Company, Schenectady, N.Y.

[21] Appl. No.: 437,937

[22] Filed: Nov. 1, 1982

[51] Int. Cl.³ .................. C07D 209/48; C07D 307/89
[52] U.S. Cl. .............................. 548/461; 260/465 H; 549/241; 548/455; 548/482
[58] Field of Search ................... 260/465 H; 548/461; 549/241; 568/44, 58

[56] References Cited

U.S. PATENT DOCUMENTS

| | | | |
|---|---|---|---|
| 3,576,882 | 4/1971 | Clark | 568/58 |
| 3,983,093 | 9/1976 | Williams et al. | 260/47 CP |
| 4,054,584 | 10/1977 | Williams | 260/346.3 |

FOREIGN PATENT DOCUMENTS 55-122757 9/1980 Japan .

Primary Examiner—Donald G. Daus
Assistant Examiner—G. Hendricks
Attorney, Agent, or Firm—Richard J. Traverso; James C. Davis, Jr.; James Magee

[57] ABSTRACT

A method for making diarylthioethers including thioetherbis(phthalic anhydrides) and thioetherbis(phthalimides) in the absence of a solvent medium by the interaction of sulfide compounds, including alkali metal sulfides and alkali metal hydrogen sulfides, with molten organo-substituted aromatic compounds including phthalic anhydrides and phthalimides mediated by a phase transfer catalyst.

14 Claims, No Drawings

SOLVENT FREE PREPARATION OF DIARYLTHIOETHERS

The present invention relates to a method of synthesizing thioethers from an interaction between a molten substituted aromatic compound and an anhydrous sulfide compound in the absence of a solvent medium. More particularly, the present invention relates to a solventless method of interacting an alkali-metal sulfide or an alkali-metal hydrogen sulfide with molten substituted phthalic anhydride, phthalimide, benzonitrile, or nitrobenzene in the presence of a phase transfer catalyst to form diarylthioethers.

Prior to the present invention a method for producing thioetherbis(phthalimides), also known as bis(thioetherphthalimides), from the conversion of N-substituted phthalimides with alkali-metal sulfides has been previously described in U.S. Pat. No. 4,054,589 and a method involving the interaction between sodium sulfide and halo-substituted phthalic anhydrides to produce thioetherbis(phthalimides) has been described previously in Japanese Pat. No. 55-122757. These methods are based on the use of dipolar aprotic solvents or nonpolar solvents with phase transfer catalysts present to facilitate reaction. Those skilled in the art know that it is often economically unattractive to effect the synthesis of various organic materials using dipolar aprotic solvents because such solvents are expensive and often subject to a variety of chemical side reactions which render them useless for recycling. Although the use of nonpolar solvents is economically attractive, methods involving the formation of thioethers utilizing nonpolar solvents to facilitate reaction produce low yields of product.

The present invention is based on the discovery that diarylthioethers of the general formula

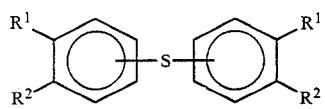

I can be made at high temperatures without the use of a dipolar aprotic solvent or a nonpolar solvent, where $R^1$ is a member selected from the group consisting of monovalent radicals of the formulas

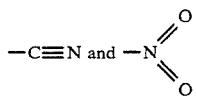

and $R^2$ is a hydrogen atom or $R^1$ and $R^2$ together define a divalent radical selected from a group of formulas consisting of

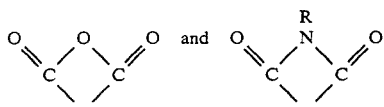

which form a cyclic structure with the phenyl group, where R is a monovalent radical selected from the group consisting of $C_{1-8}$ alkyl radicals and $C_{6-20}$ aromatic radicals.

These compounds are useful for the preparation of polyimides with high use temperatures and high oxidative stability. The yield of thioethers obtained from this process are higher than those of methods utilizing nonpolar solvents and with some thioethers, yields are higher than those of methods utilizing dipolar aprotic solvents. Obtaining high yields of diarylthioethers without the use of dipolar aprotic solvents makes the synthesis of polyidmides more economical.

There is provided by the present invention, a method for making compounds of formula I which comprises:

(a) heating a mixture of an anhydrous sulfide compound selected from the group consisting of alkali-metal sulfides of the formula $M_2S$ and alkali-metal hydrogen sulfides of the formula MHS and a member of a group consisting of substituted aromatic compounds of the formulas

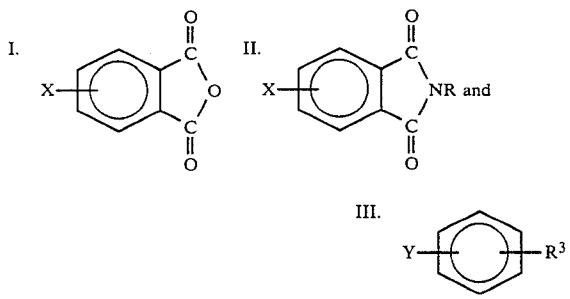

with a catalystic quantity of a phase transfer catalyst which is selected from a group consisting of phosphonium salts of the formula

ammonium salts of the formula

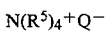

and 1, 4, 7, 10, 13, 16 hexaoxacyclooctadecane (18-crown-6) to a temperature in the range of 150° C. to 240° C. in a nitrogen atmosphere for a period ranging from 5 to 18 hours; and (b) isolating the diarylthioether product from the reaction mixture, preferably by a recrystallization procedure with an organic solvent; wherein R is as previously defined; $R^3$ is a member selected from the group consisting of monovalent radicals of the formulas

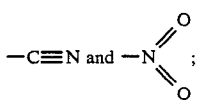

X is a monovalent radical selected from the group consisting of chloro, fluoro, bromo, iodo and nitro; Y is a monovalent radical selected from the group consisting of fluoro, bromo, chloro and iodo; $R^4$ is a monovalent radical selected from the group consisting of $C_{(1-16)}$ alkyl radicals and $C_{(6-13)}$ aromatic radicals; $R^5$ is a monovalent radical selected from the group consisting of $C_{(1-16)}$ alkyl radicals; Q is a halogen ion selected from the group consisting of bromide and chloride and M is an alkali metal selected from the group consisting of sodium, lithium and potassium.

The substituted aromatic compounds defined by formula II comprise nitrophthalic anhydrides and halophthalic anhydrides. More particularly the phthalic anhydrides of formula II include, for example, 4-chlorophthalic anhydride, 3-chlorophthalic anhydride, 4-nitrophthalic anhydride, etc. The preferred phthalic anhydrides are 4-chlorophthalic anhydride and 4-nitrophthalic anhydride.

The substituted aromatic compounds defined by formula III include N-substituted halophthalimides and N-substituted nitrophthalimides where the organic radicals R, which are bound to the nitrogen atom, include, for example, aromatic radicals such as phenyl, tolyl, xylyl, napthyl, etc. and alkyl radicals such as methyl, ethyl, propyl, butyl, pentyl, etc.

These N-substituted phthalimides can be synthesized from substituted phthalic anhydrides of formula II by effecting reaction between substantially equal moles of organic amine, $RNH_2$, and a phthalic anhydride of formula II, where R is as previously defined.

Examples of the N-substituted phthalimides defined by formula III include, for example, 4-chloro-N-methyl phthalimide, 4-nitro-N-methylphthalimide, 4-chloro-N-phenylphthalimide, 3-chloro-N-methylphthalimide, 3-chloro-N-phenylphthalimide, etc. The preferred phthalimide is 4-chloro-N-methylphthalimide which gives yields of diarylthioether 4,4'-bis(N-methylphthalimide)sulfide as high as 85% when reacted with sodium sulfide.

The substituted aromatic compounds defined by formula IV include halo-substituted benzonitriles and nitrobenzenes where Y is a halogen radical selected from the group consisting of chloro, bromo, fluoro, and iodo. Of the halo-substituted benzonitriles, 4-chloro-benzonitrile is preferred and of the halo-substituted nitrobenzenes, 4-chloro-nitrobenzene is preferred. Other compounds defined by formula IV include, for example, 3-chloro-nitrobenzene, 3-chloro-benzonitrile, and 4-bromo-benzonitrile. An example of the anhydrous alkali-metal sulfides which can be employed is, for example, sodium sulfide. An example of the anhydrous alkali metal hydrogen sulfide which can be utilized is sodium hydrogen sulfide. Commercially available anhydrous sodium sulfide may be used directly, but drying the sulfide further by azeotroping in the presence of calcium chloride is preferred.

Radicals represented by $R^4$ and $R^5$ found in the phosphonium salt and ammonium salt phase transfer catalysts as defined by formulas $P(R^4)_4{}^+Q^-$ and $N(R^5)_4{}^+Q^-$, respectively, include alkyl radicals such as, for example, butyl, phentyl, hexyl, octyl, propyl, cyclohexyl, etc. In addition, $R^4$ also includes aromatic radicals such as, for example, phenyl, etc. More particularly, the phosphonium salt and ammonium salt phase transfer catalysts include, for example, tetrabutylphosphonium bromide, tetrabutylammonium bromide, tetraphenylphosphonium bromide, tetracyclohexylphosphonium bromide, tetrapropylammonium bromide, tetrabutylphosphonium chloride, and tetrabutylammonium chloride, etc.

The preferred phase transfer catalysts are 18-crown-6 and the phosphonium salts tetrabutylphosphonium bromide and tetraphenylphosphonium bromide. Products found in reaction samples utilizing ammonium salt catalysts indicate that a substantial amount of ammonium salt decomposes during the reaction. The phosphonium salts are not as succeptable to such decomposition, permitting higher yields of desired product than the corresponding ammonium salt. In addition, phosphonium salts which experience steric hinderance such as tetracyclohexylphosphonium bromide, do not exhibit the effectiveness of phosphonium salts with simple organic radicals such as tetrabutylphosphonium bromide.

It was found that the presence of small quantities of dipolar aprotic solvents (100:65 molar ratio of anhydrous sulfide compound to solvent) such as dimethylformamide under reaction conditions provides effective catalysis, producing yields of product as high as 65%.

Although not wishing to be bound by theory, it is believed that the product yields obtained from this process are dependent on the solubility of the sulfide anion within the reaction mixture. The reaction temperature, phase transfer catalyst, the polarity of the molten substituted aromatic compound and the polarity of the diarylthioether product all effect the solubility of the sulfide anion and hence the product yields. Increasing the reaction temperatures increases the sulfide anion solubility and generally produces higher yields. Substituted aromatic compounds of high polarity provide an environment of high solubility for the sulfide anion and generally produce high yields of product, particularly when the diarylthioether formed is of high polarity. At high concentrations of catalyst the polarity of the reaction mixture is affected, therefore polar catalysts are also preferred to obtain high yields. The product yields are also believed to be dependent on the stability of the phase transfer catalyst utilized. Certain catalysts degrade in the presence of sulfide ion, producing side reactions with the reactants and a reduced product yield. Catalysts which exhibit resistance to this decomposition, such as tetrabutylphosphonium bromide, were found to produce high yields.

The reaction between the substituted aromatic compounds defined by formulas II, III and IV and the anhydrous sulfide compounds defined above can be effected at a temperature preferably in the range of 140° C. to 240° C. A two-fold molar excess of the substituted aromatic compound utilized is preferred so as to reduce the viscosity of the reaction media and maintain the polarity of the mixture as the diarylthioethers of formula I are formed. This permits the substituted aromatic compounds to function as a solvent and reactant. The quantity of phase transfer catalyst utilized is based on the number of moles of anhydrous sulfide compound present. A mole ratio of sulfide compound to phase transfer catalyst equal to 10:1 is preferred.

The products defined by formula I can be recovered from the reaction mixture by filtration. However, to obtain a sample of the products with fewer impurities the products are recrystallized from organic solvents such as, for example, dimethylformamide, dry o-dichlorobenzene and methanol. The preferred recrystallization procedure is to add o-dichlorobenzene to the reaction mixture, heat to a temperature between 130° C. and 180° C., filter, cool to 25° C. and allow the solution to stand at 25° C. for a period ranging between 14 and 25 hours. The desired product is then separated from solution by filtration.

In order that those skilled in the art may better understand how the present invention may be practiced, the following examples are given by way of illustration and not by way of limitation.

EXAMPLE 1

A mixture of 4-chlorophthalic anhydride (2.0 g, 0.011 mol), a sodium sulfide (0.21 g, 0.0027 mol), and tetrabutylphosphonium bromide (0.13 g, 0.0038 mol) was heated in a nitrogen atmosphere to 115° C. until a molten suspension of sodium sulphide was obtained. The reaction mixture was then heated to 190° C. to 200° C. for 12 hours. Isolation of the product was accomplished by adding dry o-dichlorobenzene (20 ml) with 2 ml of ethyl bromide to the reaction mixture and allowing it to cool to 25° C. Ethyl bormide serves the function of terminating thioetherbisphthalimide formation by reacting with excess sodium sulfide. Solid 4,4'-bis(phthalic anhydride)sulfide was filtered from this solution after 24 hours at 25° C. The isolated yield was 63% product having a melting point of 95° C.

The use of the catalyst 18-crown-6 (0.12 g, 0.00046 mol) under the same conditions resulted in a 68% yield of 4,4'-bis(phthalic anhydride)sulfide.

The use of more tetrabutylphosphonium bromide catalyst (0.26 g, 0.00076 mol), added in two portions 18 hours apart, increased the yield to 70%.

EXAMPLE 2

A mixture of 4-chloro-N-methylphthalimide (4.0 g, 0.021 mol), sodium sulfide (0.40 g, 0.0051 mol), and tetrabutylphosphonium bromide (0.13 g, 0.0004 mol) were heated in a nitrogen atmosphere to 160° C. for 18 hours. The product was isolated by adding dimethylformamide (20 ml) and ethyl bromide (2 ml) to the reaction mixture, heating to reflux, then filtering and allowing the mixture to stand for 14 hours at 25° C. Ethyl bromide serves the function of reacting with excess sodium sulfide so that thioetherphthalimide formation terminates. Solid 4,4'-bis(N-methylphthalimide)sulfide with a melting point of 240° C. was collected by filtration. The isolated yield was 80%. The use of 18-crown-6 (0.08 g, 0.0003 mol) at 200° C. with the same quantity of reactants produced an isolated yield of 75% 4,4'-bis(N-methylphthalimide)sulfide.

EXAMPLE 3

A mixture of 4-chlorobenzonitrile (3.0 g, 0.022 mol) sodium sulfide (0.43 g, 0.0055 mol) and tetrabutylphosphonium bromide (0.13 g, 0.00038 mol) was slowly heated to 150° C. in a nitrogen atmosphere and maintained at this temperature for 18 hours. The product was isolated by recrystallization from methanol with 2 ml of ethylbromide. The ethyl bromide terminated the formation of 4,4'-bis(cyanophenyl)sulfide. Solid 4,4'-bis(cyanophenyl)sulfide was collected in 45% yield.

The use of 18-crown-6 (0.098 g, 0.00037 mol) under these conditions produced a yield of 75%.

The use of a larger quantity of tetrabutylphosphonium bromide (2:1 mole ratio of sodium sulfide to catalyst) at 160° C. increased the yield to 75%.

EXAMPLE 4

A mixture of 4-chloronitrobenzene (1.46 g, 0.0127 mol), sodium sulfide (0.25 g, 0.0032 mol) and tetrabutylphosphonium bromide (0.108 g, 0.00277 mol) was heated to 220° C. for 18 hours in a nitrogen atmosphere. The reaction mixture was then added to dimethylformamide/ethylbromide solution and examined by HPLC methods, which indicated a 45.5% yield of 4,4'-bis(P-nitrophenyl)sulfide. The ethyl bromide serving to stop the formation of 4,4'-bis(P-nitrophenyl)sulfide. Where 18-crown-6 was utilized under the same conditions a 25% yield of 4,4'-bis(P-nitrophenyl)sulfide was obtained.

EXAMPLE 5

A series of reactions were completed with different aryl halides under the same reaction conditions to compare the yield of diarylthioethers from various aryl halides. A four to one molar ratio of aryl halide to sodium sulfide was maintained in each reaction vessel along with a 10 to 1 molar ratio of sodium sulfide to catalyst. The reactions were carried out at 200° C. for 18 hours. Set out in Table I is a summary of the different yields of diarylthioethers obtained from the various arylhalides under the same reaction conditions.

TABLE I

Percentage Yields of Thioethers from Melt Procedures

| Substrate | Percentage Yields from Use of | |
|---|---|---|
|  | 18-Crown-6 | $(P(C_4H_9)_4^+B_r^-$ |
| 4-chloro-N—methylphthalimide | 75 | 84 |
| 4-chlorophthalic anhydride | 70 | 54 |
| 4-nitro-N—methylphthalimide | 26 | 19 |
| 4-chlorobenzonitrile | 60 | 77 |
| 4-chloronitrobenzene | 25 | 46 |

As illustrated by the above data the highest yield of product was obtained with 4-chloro-N-methylphthalimide where the catalyst tetrabutylphosphonium bromide was utilized.

EXAMPLE 6

A series of reactions between sodium sulfide and 4-chloro-N-methylphthalimide were carried out using a variety of catalysts and reaction temperatures to determine the effect the catalyst and temperature have on the product yields of 4,4'-bis(N-methylphthalimide)sulfide. To each of 8 reaction vessels were added 4-chloro-N-methylphthalimide (1.00 g, 0.0051 mol) and sodium sulfide (0.10 g, 0.00128 mol). Equal amounts of various catalysts (0.00095 mol) were added to 7 of these vessels. Six of these 8 vessels were heated to approximately 200° C. in a nitrogen atmosphere for 18 hours. Two vessels containing tetrabutylphosphonium bromide catalysts were heated to 225° C. and 160° C., respectively. The mixtures were then similarly prepared for examination by high pressure liquid chromatography (HPLC). Set out in Table II is a summary of the yields produced from utilizing different catalysts and temperatures.

TABLE II

Effect of Catalyst Type and Temperature On Yields of 4,4-Bis(N—Methylphthalimide)Sulfide

| Catalyst | Temperature (°C.) | Reaction Time | Percentage Yield |
|---|---|---|---|
| Tetrabutylphosphonium bromide | 225 | 6 h | 84 |
| Tetrabutylphosphonium bromide | 160 | 16 h | 80 |
| Tetraphenylphosphonium bromide | 200 | 18 h | 76 |
| Tetracyclohexylphosphonium bromide | 200 | 18 h | 44 |
| Tetrabutylammonium bromide | 200 | 18 h | 34 |
| Dimethylformamide | 200 | 18 h | 65 |
| No Catalyst | 200 | 18 h | 10 |
| 18-Crown-6 | 210 | 18 h | 75 |

As illustrated by the above data, the highest yield of 4,4'-bis(N-methylphthalimide)sulfide was obtained utilizing tetrabutylphosphonium bromide at a high temperature. The data also indicated that dimethylformamide is an effective catalyst for this process.

EXAMPLE 7

A mixture of 4-nitro-N-methylphthalimide (1.5 g, 0.00728 mol) sodium sulfide, (0.155 g, 0.00199 mol) and tetrabutylphosphonium bromide (0.06 g, 0.000177 mol) were slowly heated to 205° C. in a nitrogen atmosphere (2 hours) and held at this temperature for 18 hours. The mixture solidified at 160° C. and remained solid during the reaction time. The product was isolated by adding dry o-dichlorobenzene (100 ml) containing 2 ml of ethylbromide and heated to 180° C. The ethylbromide serving to stop the formation of thioetherbis(phthalimides). The yield of 4,4'-bis(N-methylphthalimide)sulfide was 26% as determined by HPLC methods.

It should be understood that the above examples represent only a limited number of the diarylthioethers which can be made in accordance with the practice of the invention which are shown by formula I.

What I claim as new and desire to secure by Letters Patent of the United States is:

1. A method for making diarylthioethers of the formula

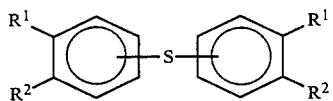

which comprises:

(a) heating a mixture of an anhydrous sulfide compound selected from the group consisting of alkalimetal sulfides of the formula and alkali metal hydrogen sulfides of the formula

MHS and a member selected from a group consisting of molten substituted aromatic compounds of the formulas

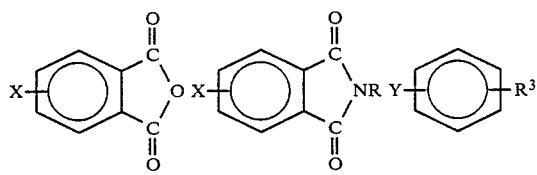

in the presence of a catalytic quantity of phase transfer catalyst selected from a group consisting of phosphonium salts of the formula $P(R^4)_4{}^+Q^-$ and ammonium salts of the formula $N(R^5)_4{}^+Q^-$ and 18-crown-6 to a temperature within the range 140° C. to 240° C. in a nitrogen atmosphere in the absence of a solvent medium for a period ranging from 5 to 18 hours; and (b) recovering the diarylthioether product from said mixture, where $R^1$ is a member selected from the group consisting of monovalent radicals of the formulas

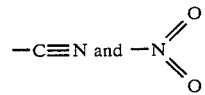

and $R^2$ is a hydrogen atom or $R^1$ and $R^2$ together define a divalent radical of a formula selected from the group consisting of

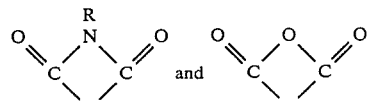

which form a cyclic structure with the phenyl group, where R is a monovalent radical selected from the group consisting of $C_{1-8}$ alkyl radicals and $C_{6-20}$ aromatic radicals;

$R^3$ is a member of a group of monovalent radicals of the formulas

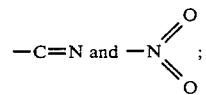

$R^4$ is a monovalent radical selected from the group consisting of $C_{1-16}$ alkyl radicals and $C_{6-13}$ aromatic radicals;

$R^5$ is a monovalent radical selected from the group $C_{1-16}$ alkyl radicals;

X is a monovalent radical selected from the group consisting of chloro, fluoro, bromo, iodo and nitro;

Y is a monovalent radical selected from the group consisting of fluoro, bromo, iodo, and chloro;

Q is a halogen ion selected from the group consisting of bromide and chloride; and M is an alkali metal selected from the group sodium, lithium and potassium.

2. A method in accordance with claim 1 where said anhydrous sulfide compound is sodium sulfide.

3. A method in accordance with claim 1 where said catalyst is selected from the group consisting of tetrabutylphosphonium bromide, tetraphenylphosphonium bromide and 18-crown-6.

4. A method in accordance with claim 1 where the molar ratio of the substituted aromatic compounds to the anhydrous sulfide compound is 4 to 1.

5. A method in accordance with claim 1 where the molar ratio of anhydrous sodium compound to phase transfer catalyst is 10 to 1.

6. A method in accordance with claim 1 further including the step of adding a second charge of catalyst to said mixture during the course of the reaction.

7. A method in accordance with claim 1 wherein said substituted aromatic compound is 4-chloronitrobenzene.

8. A method in accordance with claim 1 wherein said substituted aromatic compound is 4-nitro-N-methylphthalimide.

9. A method in accordance with claim 1 wherein said aromatic compound is selected from the group consisting of 4-chloro-N-methylphthalimide, 4-chlorophthalic anhydride and 4-chlorobenzonitrile.

10. A method in accordance with claim 1 where said diarylthioether produce is recovered from said mixture by recrystallization from an organic solvent selected from the group consisting of o-dichlorobenzene, dimethylformamide and methanol.

11. A method for making 4,4'-bis(N-methylphthalimide)sulfide which comprises:
   (a) heating a mixture of anhydrous sodium sulfide and molten 4-chloro-N-methylphthalimide and an effective amount of tetrabutylphosphonium bromide to 160° C. for 18 hours in the absence of solvent; and
   (b) isolating the 4,4'-bis(N-methylphthalimide)sulfide from said mixture.

12. A method for making 4,4'-bis(phthalic anhydride)sulfide which comprises:
   (a) heating a mixture of sodium sulfide and molten 4-chlorophthalic anhydride and an effective amount of phase transfer catalyst selected from the group consisting of tetrabutylphosphonium bromide and 18-crown-6 to a temperature in the range of 180° C. to 200° C. for 12 hours in the absence of solvent, and
   (b) isolating the 4,4'-bis(phthalic anhydride)sulfide from said mixture.

13. A method for making 4,4'-bis(N-methylphthalimide)sulfide which comprises:
   (a) heating a mixture of anhydrous sodium sulfide and molten 4-nitro-N-methylphthalimide and an effective amount of tetrabutylphosphonium bromide to 205° C. for 18 hours without a solvent and
   (b) isolating the 4,4'-bis(N-methylphthalimide)sulfide from said mixture.

14. A method of making diarylthioethers of the formula

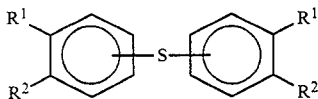

which comprises:
   (a) heating a mixture of an anhydrous sulfide compound selected from the group consisting of alkali metal sulfides of the formula $M_2S$ and alkali metal hydrogen sulfides of the formula MHS and a member of the group of molten substituted aromatic compounds of the formulas

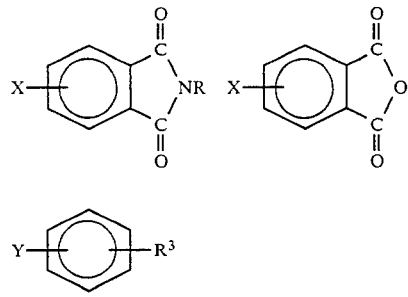

in the presence of a catalytic quantity of dimethylformamide at a temperature within the range of 140° C. to 240° C. in a nitrogen atmosphere in the absence of a solvent medium for a period ranging from 5 to 18 hours; and
   (b) isolating the diarylthioether product from said mixture, where $R^1$ is a member selected from the group consisting of monovalent radicals of the formulas

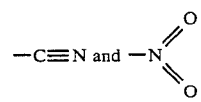

and $R^2$ is hydrogen or $R^1$ and $R^2$ together define a divalent radical of a formula selected from the group consisting of

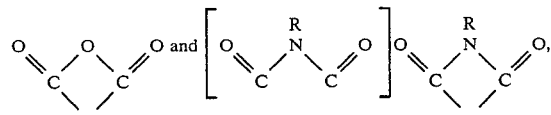

which form a cyclic structure with the phenyl group, where R is a monovalent radical selected from the group consisting of $C_{1-8}$ alkyl radicals and $C_{6-20}$ aromatic radicals;
$R^2$ is a hydrogen atom or combined with $R^1$ to form a divalent radical as previously described;
$R^3$ is a member of group of monovalent radicals of the formulas

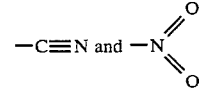

X is a monovalent radical selected from the group consisting of chloro, fluoro, bromo, iodo and nitro;
Y is a monovalent radical selected from the group consisting of fluoro, bromo, iodo, and chloro;
M is an alkali metal selected from the group consisting of sodium, lithium and potassium.

* * * * *

UNITED STATES PATENT AND TRADEMARK OFFICE
CERTIFICATE OF CORRECTION

PATENT NO. : 4,499,285
DATED : February 12, 1985
INVENTOR(S) : Thomas L. Evans

It is certified that error appears in the above-identified patent and that said Letters Patent is hereby corrected as shown below:

Column 7, line 36,    insert  -- $M_2S$ --

Column 8, line 25,    delete "-C=N" and insert -- $-C\equiv N$ --

Column 8, line 68,    delete "produce" and insert  -- product --

Column 10, line 35,   delete

"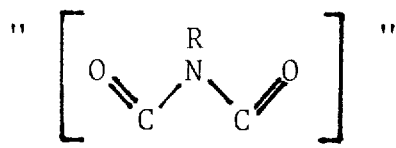"

Signed and Sealed this

Sixth Day of August 1985

[SEAL]

Attest:

DONALD J. QUIGG

Attesting Officer   Acting Commissioner of Patents and Trademarks